United States Patent [19]

Hiraoka et al.

[11] Patent Number: 5,894,083
[45] Date of Patent: Apr. 13, 1999

[54] CONTINUOUS GAS ANALYZER

[75] Inventors: Shusuke Hiraoka, Shiga; Katsuhiko Araya, Kyoto; Hiroaki Matsuhisa, Kyoto; Yoshihide Kanki, Kyoto; Hiroshi Murakami, Kyoto, all of Japan

[73] Assignee: Shimadzu Corporation, Kyoto, Japan

[21] Appl. No.: 08/845,924

[22] Filed: Apr. 28, 1997

[30] Foreign Application Priority Data

Apr. 30, 1996 [JP] Japan ................................ 8-134480

[51] Int. Cl.$^6$ ........................................... G01N 7/00
[52] U.S. Cl. ............................................. 73/23.2
[58] Field of Search ........................ 73/1.07, 23.2, 73/864.81; 364/571.01; 422/83, 62; 340/632

[56] References Cited

U.S. PATENT DOCUMENTS 4,869,874  9/1989  Falat .................................. 422/53
4,921,886  5/1990  Ewan et al. ....................... 423/235
5,242,836  9/1993  Rose .............................. 73/23.2 X
5,469,369  11/1995  Rose-Pehrsson et al. ........ 73/23.2

Primary Examiner—Hezron E. Williams
Assistant Examiner—Jay L. Politzer
Attorney, Agent, or Firm—Nikaido, Marmelstein, Murray & Oram LLP

[57] ABSTRACT

A standard gas introduction passage and an air inlet port are provided on positions downstream and upstream a dehumidifier respectively. A zero gas and a span gas are measured in dry states, a value of the atmosphere introduced from the air inlet port which is measured in the same moisture concentration as the sample gas is subtracted as a moisture interference value from the measured value of the sample gas for correcting moisture interference, and calibration curve data are applied to a result of measurement after the correction. Calibration can be finished in a short period, whereby the capacities of standard gas cylinders can be reduced and the overall device can be miniaturized.

5 Claims, 7 Drawing Sheets

CONTINUOUS GAS ANALYZER

BACKGROUND OF THE INVENTION

1. Field of the Invention

The present invention relates to a continuous gas analyzer for continuously analyzing a target gas component contained in a sample gas, and more particularly, it relates to an analyzer such as an $SO_2$ measuring device for analyzing a component which is exposed to interference by moisture.

2. Description of the Background Art

FIG. 1 shows a conventional $SO_2$ measuring device. A sample gas introduction passage 6 for sucking a sample gas by a suction pump 2 and introducing the same into an analyzer 4 is provided with a flow control valve 8 on a position upstream the pump 2, while a dehumidifier 10 is provided between the pump 2 and the analyzer 4 as a constant humidity device for keeping the moisture concentration in the sample gas at a constant level. A standard gas introduction passage 14 is connected to the passage between the pump 2 and the dehumidifier 10 through a three-way cock 12. The standard gas introduction passage 14 is connected with cylinders 16 and 18 of a zero gas containing no $SO_2$ and a span gas containing $SO_2$ in a constant concentration through switching valves 20 and 22 respectively. The three-way cock 12 is switched and the switching valves 20 and 22 are opened/closed for switching and introducing the sample, zero and span gases into the analyzer 4 through the dehumidifier 10.

The analyzer 4 comprises a data processing part having a calibration curve storage part for holding measured values of the zero and span gases supplied from the standard gas introduction passage 14 as calibration curve data for calculating the sample gas concentration on the basis of the calibration curve data.

In relation to measurement of $SO_2$, a detection part of the analyzer 4 also has sensitivity to moisture. Therefore, moisture positively acts on detected values as moisture interference.

In calibration, the three-way cock 12 and the switching valves 20 and 22 are switched to introduce the zero and span gases into the analyzer. At this time, the standard gases are also supplied with moisture of a constant concentration from the dehumidifier 10. Thus, moisture interference constantly acts between zero and a span value.

FIG. 2 shows the relation between calibration curves and moisture interference. When the zero and span gases are guided to the analyzer 4 through the dehumidifier 10, a calibration curve (b) is formed due to positively oriented indication by moisture interference. Due to calibration in a wet state containing moisture at zero and span points, however, an apparent calibration curve (a) passes through the origin after the calibration. Namely, it comes to that the calibration is made with addition of the moisture interference.

When the target gas component is $SO_2$ which is exposed to moisture interference, the speed of response of the sample gas is retarded due to adsorption of the target gas component by the moisture in a wet state, and hence the calibration time is increased. Consequently, the zero and span gases are consumed in large amounts and the capacities of the standard gas cylinders cannot be reduced, to hinder miniaturization of the overall device.

SUMMARY OF THE INVENTION

An object of the present invention is to miniaturize the overall device by reducing the capacities of standard gas cylinders by making it possible to finish calibration in a short time.

The present invention provides a continuous gas analyzer comprising a detection part for detecting a target gas component, a sample gas introduction passage for guiding a sample gas to the detection part through a constant humidity device for adjusting the moisture concentration of the sample gas to a constant level, a standard gas introduction passage which can switch and supply a zero gas containing no target gas component and a span gas containing the target gas component in a constant concentration and is connected to the sample gas introduction passage through a switching valve, and a data processing part having a calibration curve storage part for holding measured values of the zero and span gases supplied from the standard gas introduction passage as calibration curve data for calculating the sample gas concentration on the basis of the calibration curve data. A connecting position for the standard gas introduction passage and the sample gas introduction passage is set between the constant humidity device and the detection part. The sample gas introduction passage is provided with an air inlet port which can introduce the atmosphere substitutionally for the sample gas on a position upstream the constant humidity device. The data processing part comprises the calibration curve storage part for holding values of the zero and span gases measured in dry states as the calibration curve data. The data processing part further comprises a moisture interference correction part for subtracting a measured value of the atmosphere introduced from the air inlet port as a moisture interference value from the measured value of the sample gas, while an operation part of the data processing part calculates the target gas component by applying the calibration curve data of the calibration curve storage part to a result of measurement obtained by correcting the moisture interference.

According to the present invention, the values of the zero and span gases measured in dry states are employed as the calibration curve data and the value of the atmosphere introduced from the air inlet port and measured in the same moisture concentration as the sample gas is employed as the moisture interference value to be subtracted from the measured value of the sample gas for carrying out moisture interference correction and applying the calibration curve data to the result of measurement obtained with correction of the moisture interference, thereby calculating the target gas component. Thus, the calibration is performed in a dry state, whereby the standard gases are not adsorbed by moisture, the times for feeding the standard gases are shortened as compared with calibration in a wet state, consumption of the standard gases is reduced, employed gas cylinders can be reduced in size, and the overall analyzer can be miniaturized.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Figure 1:
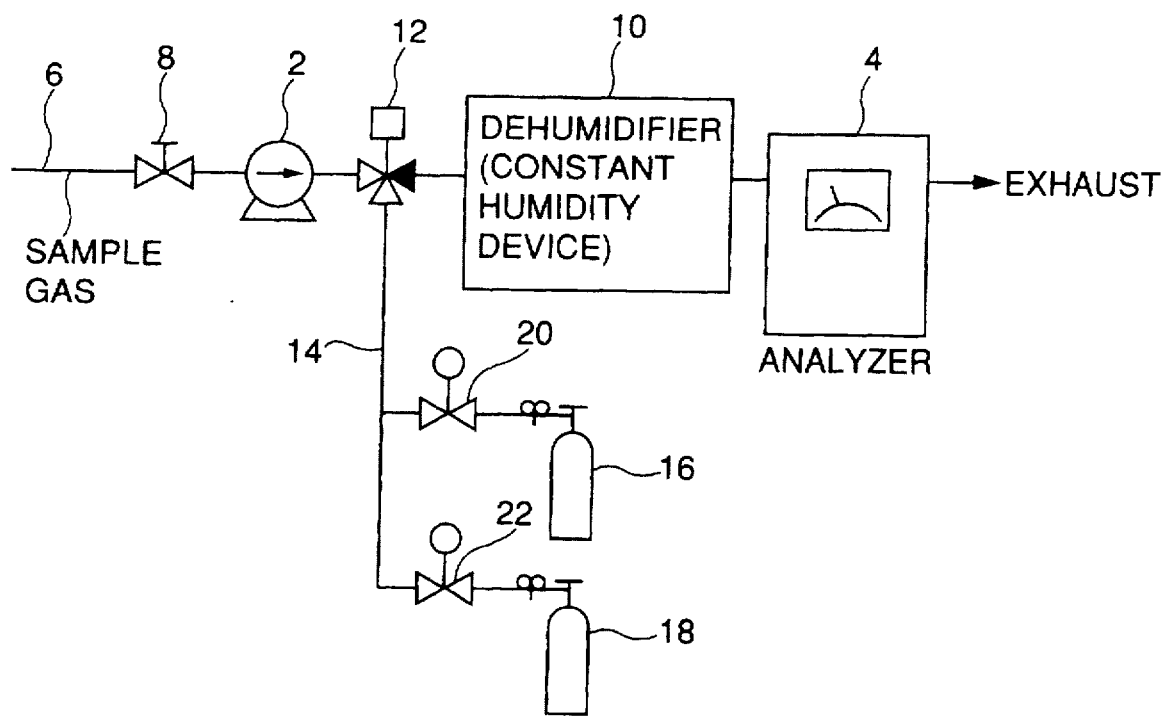
FIG. 1 is a passage diagram showing a conventional $SO_2$ measuring device.
Figure 2:
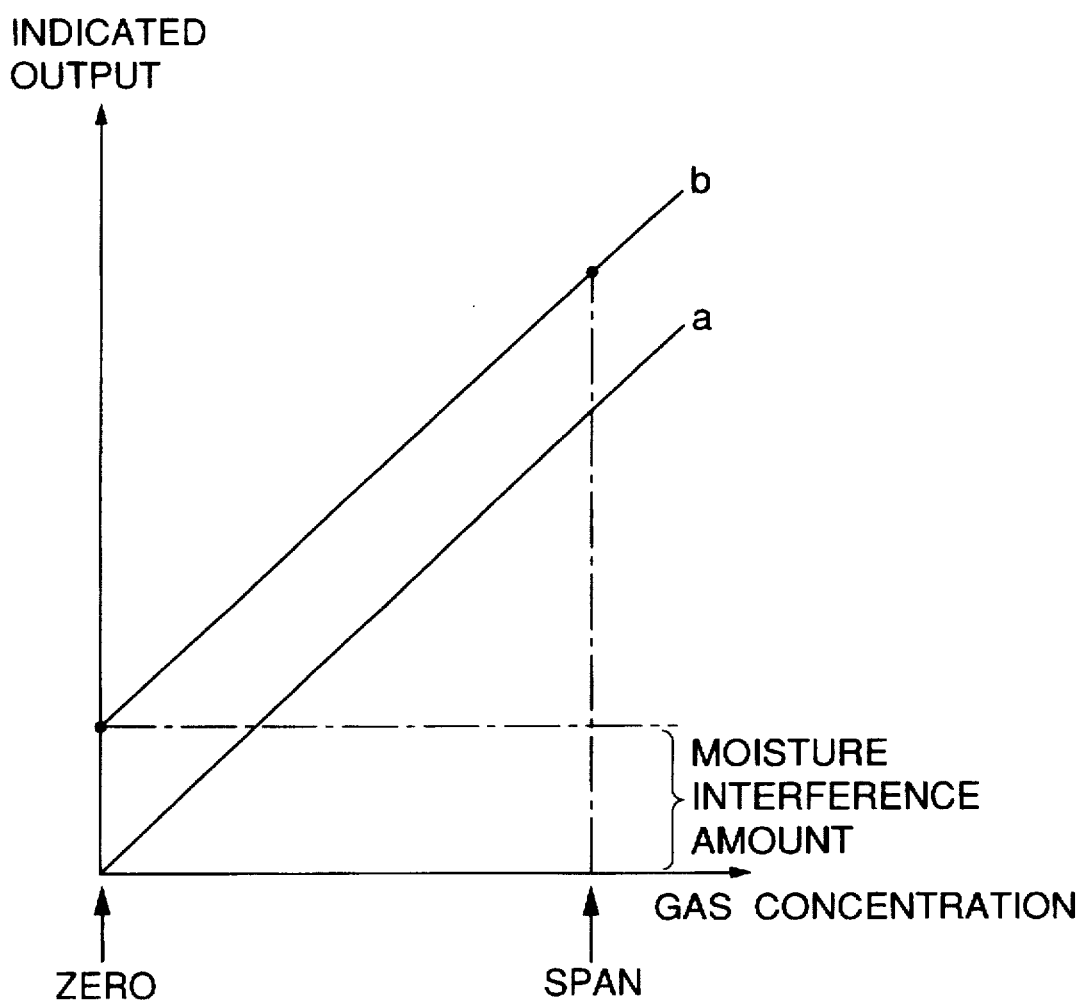
FIG. 2 shows the relation between calibration curves and moisture interference.
Figure 3:
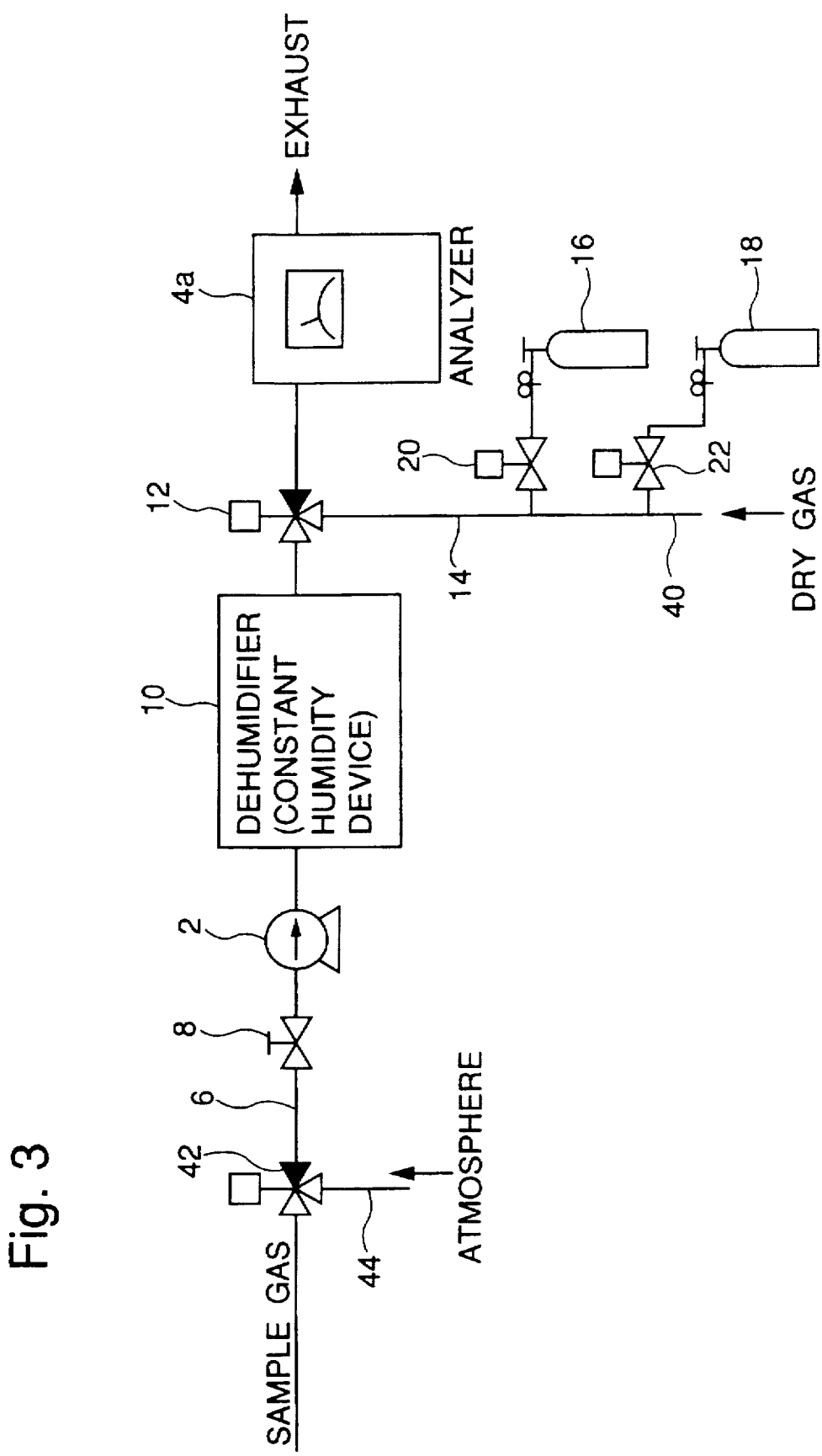
FIG. 3 is a passage diagram showing an $SO_2$ measuring device according to an embodiment of the present invention.

FIG. 3 illustrates the overall structure of an $SO_2$ measuring device according to an embodiment of the present invention. Referring to FIG. 3, members identical to those in FIG. 1 are denoted by the same reference numerals. A sample gas introduction passage 6 for sucking a sample gas by a suction pump 2 and introducing the same into an analyzer 4a is provided with a flow control valve 8 on a position upstream the pump 2, while a dehumidifier 10 is provided between the pump 2 and the analyzer 4a as a constant humidity device for keeping the moisture concentration in the sample gas at a constant level.

A three-way cock 12 which is a connection part between a standard gas introduction passage 14 and the sample gas introduction passage 6, which has been positioned upstream the dehumidifier 10 in FIG. 1, is positioned downstream a dehumidifier 10, i.e., between the dehumidifier 10 and the analyzer 4a in this embodiment. Cylinders 16 and 18 of a zero gas containing no $SO_2$ and a span gas containing $SO_2$ in a constant concentration respectively are connected to the standard gas introduction passage 14 through switching valves 20 and 22 respectively, while a dry gas passage 40 which can supply a dry gas through a switching valve is further connected to the standard gas introduction passage 14.

An air inlet port 44 which can introduce the atmosphere is connected to the sample gas introduction passage 6 through a three-way cock 42 on a position upstream the flow control valve 8.

When the three-way cock 12 is set on the side of the standard gas introduction passage 14, the zero, span and dry gases are switched and introduced into the analyzer 4a by opening/closure of the switching valves 20 and 22 and the dry gas passage 40 without through the dehumidifier 10. When the three-way cock 12 is set on the side of the sample gas introduction passage 6, on the other hand, the sample gas and the atmosphere are switched and introduced into the analyzer 4a by switching of the three-way cock 42 through the humidifier 10.

The analyzer 4a comprises a data processing part, which has a calibration curve storage part for holding measured values of the zero and span gases supplied from the standard gas introduction passage 14 as calibration curve data for calculating the sample gas concentration on the basis of the calibration curve data.

Figure 4:
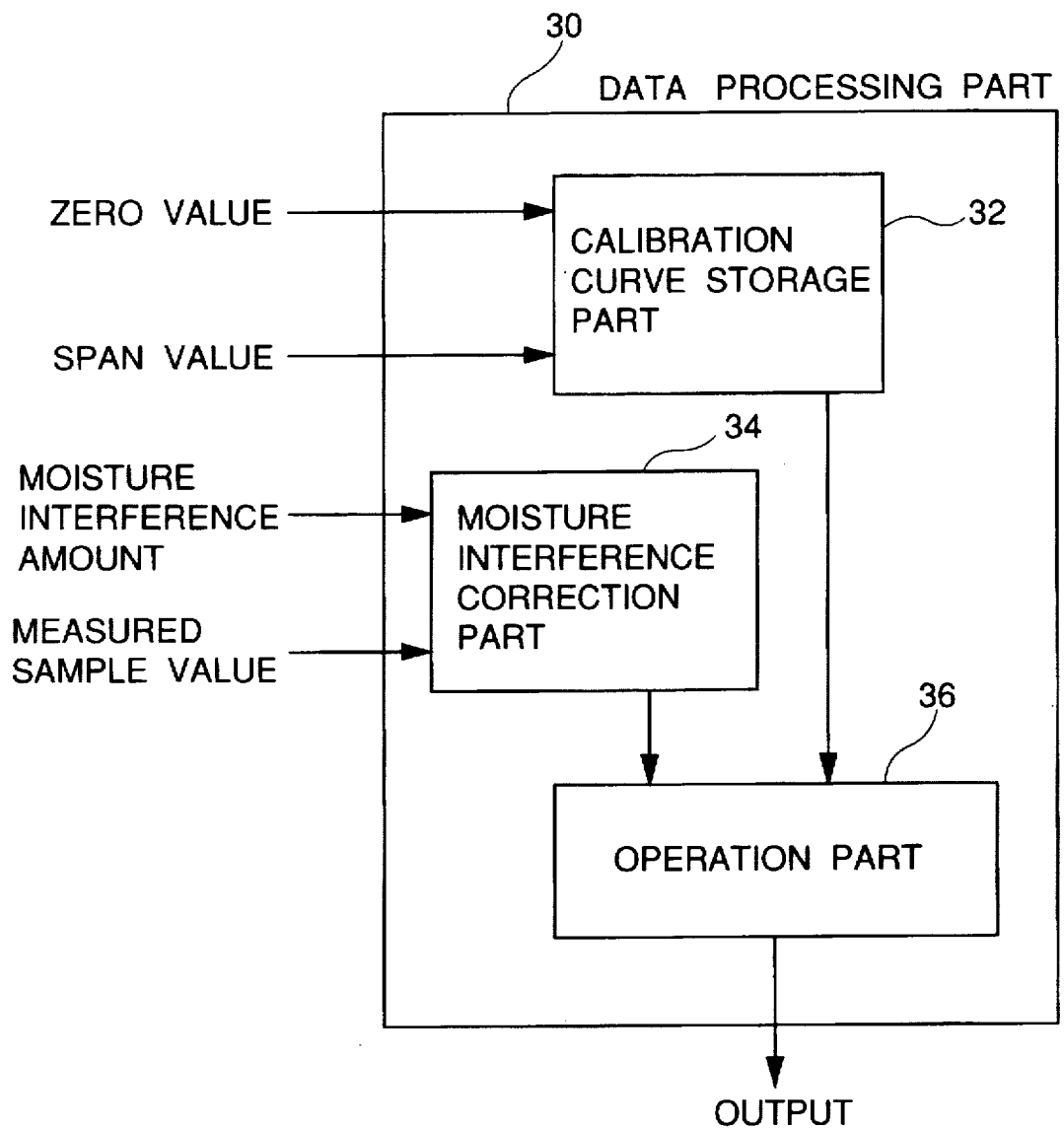
FIG. 4 is a block diagram showing a data processing part in the $SO_2$ measuring device according to the embodiment of the present invention.

FIG. 4 shows the data processing part 30, which comprises the calibration curve storage part 32, a moisture interference correction part 34 and an operation part 36. The calibration curve data storage part 32 is adapted to hold values of the zero and span gases measured in dry states. The moisture interference correction part 34 employs a measured value of the atmosphere introduced from the air inlet port 44 as a moisture interference value, and subtracts this moisture interference value from the the measured value of the sample gas. The operation part 36 applies the calibration curve data of the calibration curve storage part 32 to a result obtained by correcting moisture interference for calculating a target gas component.

Figure 5:
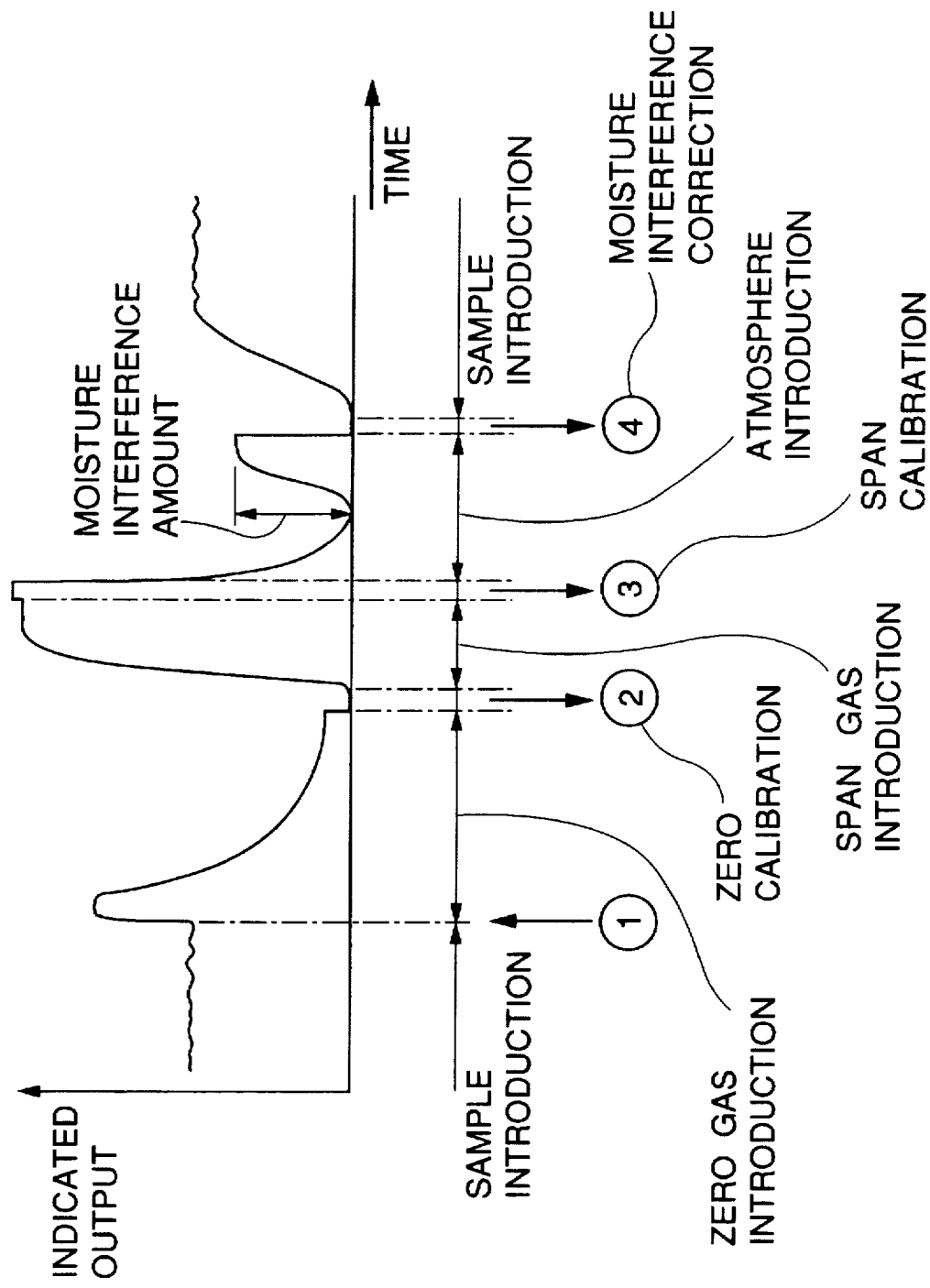
FIG. 5 is a timing chart showing the operation of the embodiment.
Figure 6:
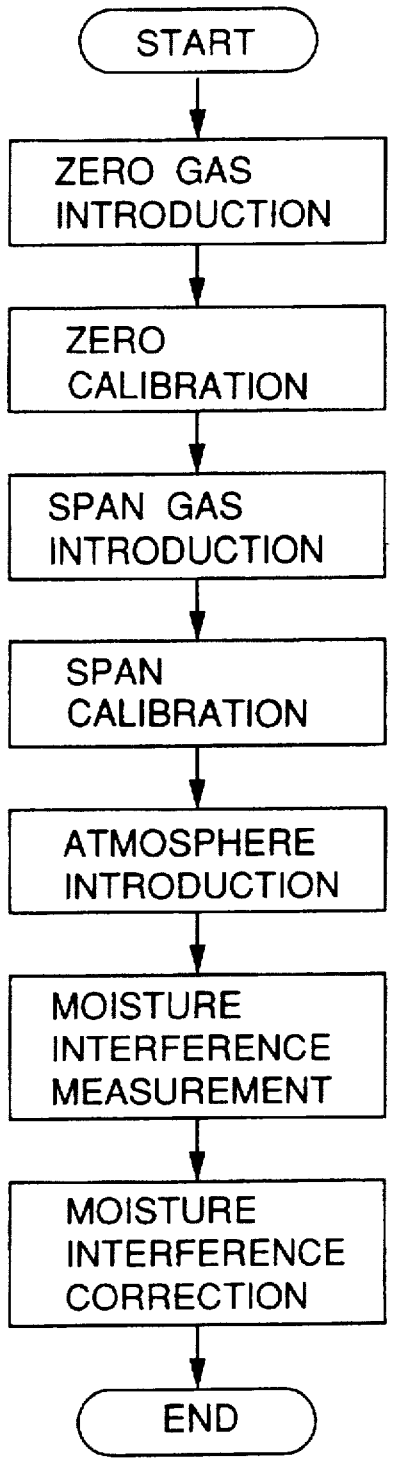
FIG. 6 is a flow chart showing calibration and moisture interference correction in the embodiment.

The operation of this embodiment is described with reference to FIGS. 5 to 7.

During sample gas measurement, the three-way cock 42 is set on a side for introducing the sample gas, while the three-way cock 12 is set on a side for introducing the sample gas into the analyzer 4a. The sample gas is sucked by the pump 2 so that its moisture content is adjusted to a constant level through the dehumidifier 10, and guided to the analyzer 4a to be subjected to analysis.

In calibration, the three-way cock 12 is switched to a side for guiding the standard gas introduction passage 14 to the analyzer 4a, the dry gas introduction passage 40 is closed, and the zero and span gases are switched by opening/closure of the switching valves 20 and 22 and introduced into the analyzer 4a.

The operation is now described in more detail. During sample measurement, the operation is switched to calibration periodically or at need. FIG. 6 shows calibration and moisture interference correction. When the operation is switched to calibration, the three-way cock 12 is switched toward the standard gas introduction passage 14, and the switching valves 20 and 22 are opened and closed respectively for introducing the zero gas into the analyzer 4a. In the calibration, a moisture interference correcting operation is canceled and an indicated output is increased by the moisture interference, as shown at ① in FIG. 5. The indicated output is reduced as the interior of a pipe of the analyzer 4a is dried, finally to be grought to a zero point after drying. Thus, zero calibration is completed (② in FIG. 5).

Then, the switching valves 20 and 22 are closed and opened respectively for introducing the span gas into the analyzer 4a, and the indicated output is brought to a span point when the indication is stabilized. Thus, span calibration is completed (③ in FIG. 5).

The three-way cock 12 is switched again to connect the sample gas introduction passage 6 to the analyzer 4a and the three-way cock 42 is switched toward the air inlet port 44, so that the pump 2 sucks the atmosphere. The sucked atmosphere is introduced into the analyzer 4a while its moisture content is adjusted to a constant level by the dehumidifier 10. While the indication of the atmosphere containing no target gas component must be zero, indication appears on a positive side due to moisture interference. This indication is shifted to zero so that the amount of moisture interference is subtracted from the sample indication. Thus, moisture interference correction is completed (④ in FIG. 5).

Figure 7:
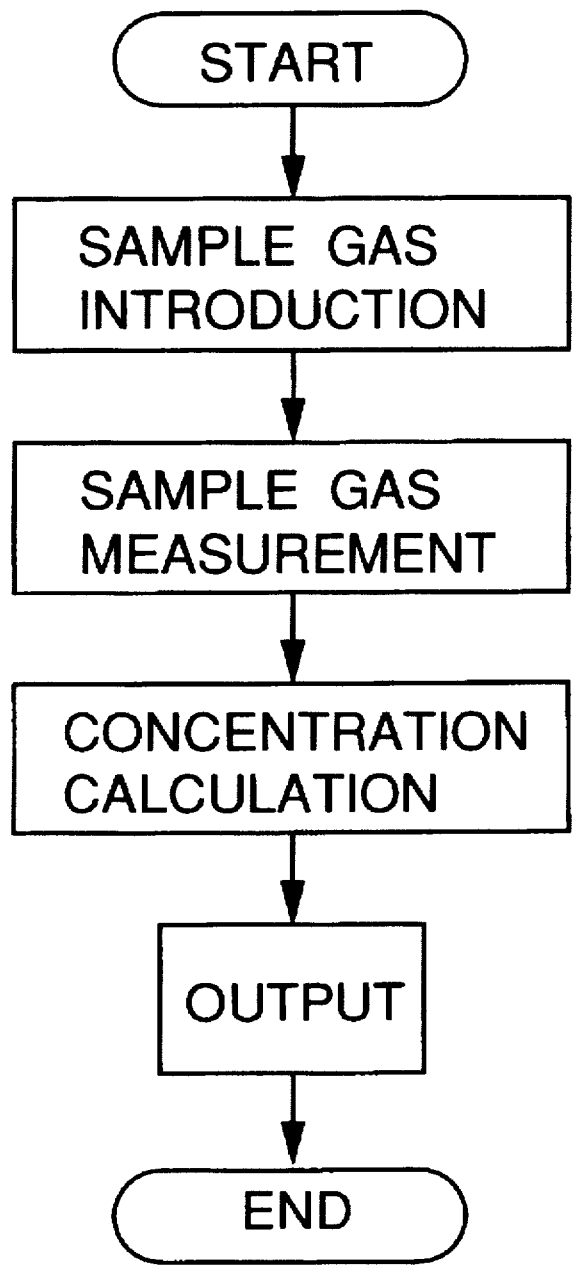
FIG. 7 is a flow chart showing a sample measuring operation in the embodiment.

When the calibration and moisture interference correction are completed, the operation is returned to measurement of the sample gas, as shown in FIG. 7. The amount of moisture interference is already subtracted from the measured value of the sample gas, and hence the calibration curve data are applied to the measured value for calculating and outputting the target gas component concentration.

The dry gas introduction passage 40 is connected to the standard gas introduction passage 14 in the embodiment shown in FIG. 3, whereby the dry gas can substitute for the zero gas for drying the interior of the pipe in the calibration. Thus, no zero gas is consumed for drying the pipe, whereby the zero gas cylinder can be miniaturized. In this case, the zero and span gases are equal in consumption to each other.

When the interior of the pipe is dried with the zero gas as described above, no dry gas introduction passage 40 is necessary.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A continuous gas analyzer, comprising:

detection means for detecting a target gas component;

sample gas introduction means for guiding a sample gas to said detection means through a constant humidity means for adjusting the moisture concentration of the sample gas to a constant level;

standard gas introduction means, capable of switching and supplying a zero gas containing no target gas component and a span gas containing the target gas component in a constant gas concentration, said standard gas introduction means being connected to said sample gas introduction means through a first switching valve means; and data processing means having a calibration curve storage means for holding measured values of the zero and span gases being supplied from the standard gas introduction means as calibration curve data for calculating the sample gas concentration based upon the calibration curve data, wherein a connecting position for said standard gas introduction means and said sample gas introduction means is located between the constant humidity means and the detection means, wherein said sample gas introduction means is provided with an air inlet port means for introducing the atmosphere substitutionally for the sample gas at a position upstream of said constant humidity means, and wherein the calibration curve storage means of the data processing means holds values of the zero and span gases measured in dry states as the calibration curve data, said data processing means further comprises a moisture interference correction means for subtracting a measured value of the atmosphere being introduced from the air inlet port means as a moisture interference value from the measured value of the sample gas, and wherein an operation means of said data processing means calculates concentration of the target gas component by applying the calibration curve data of the calibration curve storage means to a result of a measurement being obtained by correcting moisture interference.

2. A continuous gas analyzer as recited in claim 1, wherein said standard gas introduction means is connected with a dry gas means for supplying a dry gas through a second switching valve means.

3. A continuous gas analyzer as recited in claim 1, further comprising:

suction pump means provided on the sample gas introduction means for providing a suction therein;

flow control valve means connected to said suction pump means, said flow control valve means and the constant humidity means being configured upstream and downstream of said suction pump means, respectively, wherein said air inlet port means is connected to said sample gas introduction means through a second switching valve means, the second switching valve means being switched with the sample gas at a position upstream of the flow control means.

4. A continuous gas analyzer as recited in claim 1, wherein said constant humidity means comprises a dehumidifier means.

5. A continuous gas analyzer as recited in claim 1, wherein said sample gas comprises silicon dioxide gas.

* * * * *